United States Patent [19]

Tamura et al.

[11] Patent Number: 4,719,207
[45] Date of Patent: Jan. 12, 1988

[54] CNS ACTIVE SUBSTITUTED AZETIDINONE COMPOUNDS

[75] Inventors: Toshinari Tamura; Makoto Yoshida, both of Saitama; Shin-ichi Tsukamoto, Tokyo; Hidenori Iwamoto, Saitama; Minoru Yamamoto, Kanagawa; Soichi Kagami, Saitama, all of Japan

[73] Assignee: Yamanouchi Pharmaceutical Co., Ltd., Tokyo, Japan

[21] Appl. No.: 747,018

[22] Filed: Jun. 20, 1985

[30] Foreign Application Priority Data

Jun. 25, 1984 [JP] Japan .................. 59-129220
Jul. 17, 1984 [JP] Japan .................. 59-148173
Sep. 25, 1984 [JP] Japan .................. 59-199827
Sep. 25, 1984 [JP] Japan .................. 59-199828

[51] Int. Cl.$^4$ .................. A61K 31/415; C07D 403/12; C07D 403/14
[52] U.S. Cl. .................. 514/210; 514/397; 540/200; 540/354; 540/360; 540/362; 540/363; 548/336
[58] Field of Search .................. 540/200, 360, 354, 362, 540/363; 548/336; 514/210, 397

[56] References Cited

U.S. PATENT DOCUMENTS 4,610,821  9/1986  Tamura et al. .................. 540/200

OTHER PUBLICATIONS

*Chemical Abstracts*, 77:139047d (1972) [D. Boyd et al., *J. Am. Chem. Soc.* 1972, 94, 6513].
*Chemical Abstracts*, 85:21078b (1976) [Kamiya et al., Ger. Offen. 2,529,941, 4/8/76].
*Chemical Abstracts*, 89:129384v (1978) [Wasserman et al., Ger. Offen. 2,747,494, 5/3/78].
*Chemical Abstracts*, 92:180439f (1980) [D. Boyd et al., *Tetrahedron* 1979, 35, 1499].
*Chemical Abstracts*, 94:15455s (1981) [K. Chiba et al., *J. Chem. Soc. Chem. Commun.*, 1980, (16), 770].
*Chemical Abstracts*, 94:65461m (1981) [Hashimoto et al., U.S. Pat. No. 4,207,234, 6/10/80].

*Primary Examiner*—Richard A. Schwartz
*Attorney, Agent, or Firm*—Burgess, Ryan and Wayne

[57] ABSTRACT

Substituted azetidinone compounds are provided which have the formula:

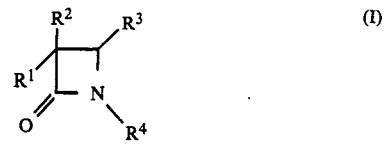

(I)

wherein one of $R^1$ and $R^2$ represents a substituted lower alkyl group, an azido group, an amino group, a lower acylamino group, a mercapto group or a lower alkylthio group and the other represents a hydrogen group, or, both represent hydrogen atoms or lower alkyl groups; $R^3$ represents a hydrogen atom or a group shown by formula:

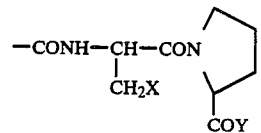

(wherein X represents

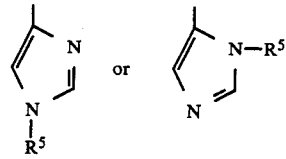

(wherein $R^5$ represents a hydrogen atom or a lower alkyl group) and Y represents a hydroxy group, a lower alkoxy group, an amino group, a mono- or di-lower alkylamino group); $R^4$ represents a hydrogen atom, a substituted or unsubstituted lower alkyl group or a group shown by formula: —CH$_2$CO—A (wherein A represents an amino group or a group shown by formula:

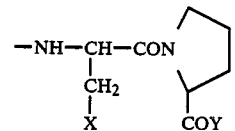

(wherein X and Y are as defined above), provided that when $R^1$ and $R^2$ are both hydrogen atoms, at least $R^4$ represents a group other than a hydrogen atom and provided that either $R^3$ or $R^4$ represents a group other than a hydrogen atom. The compounds have strong CNS action.

7 Claims, No Drawings

CNS ACTIVE SUBSTITUTED AZETIDINONE COMPOUNDS

The present invention relates to substituted azetidinone compounds, their preparation, and medicaments containing them. More particularly, the present invention relates to compounds shown by general formula (I):

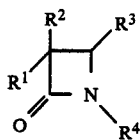

wherein one of $R^1$ and $R^2$ represents a substituted lower alkyl group, an azido group, an amino group, a lower acylamino group, a mercapto group or a lower alkylthio group and the other represents a hydrogen group, or, both represent hydrogen atoms or lower alkyl groups; $R^3$ represents a hydrogen atom or a group shown by formula:

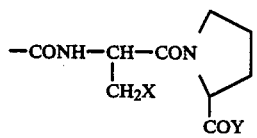

(wherein X represents

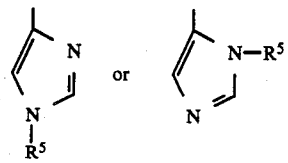

(wherein $R^5$ represents a hdrogen atom or a lower alkyl group) and Y represents a hydroxy group, a lower alkoxy group, an amino group, a mono- or di-lower alkylamino group); $R^4$ represents a hydrogen atom, a substituted or unsubstituted lower alkyl group or a group shown by formula: —CH$_2$CO—A (wherein A represents an amino group or a group shown by formula:

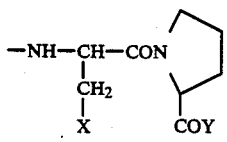

(wherein X and Y are as defined above), provided that when $R^1$ and $R^2$ are both hydrogen atoms, $R^4$ represents a group other than a hydrogen atom and provided that at least either $R^3$ or $R^4$ represents a group other than a hydrogen atom. The invention also relate to salts thereof, pocesses for producing them and medicaments containing these compounds.

The term "lower" as used in "substituted lower alkyl group", "lower alkylthio group", "lower alkyl group", "lower alkoxy group", "lower alkylamino group" or "lower acylamino group" for the substituents in the foregoing general formulae refers to a straight or branched carbon chain having 1 to 5 carbon atoms. Accordingly, the lower acylamino group includes an acetylamino group, a propionylamino group, a butyrylamino group, a pentanoylamino group, a sec-butyrylamino group, etc. The lower alkylthio group includes a methylthio group, an ethylthio group, a propylthio group, an isopropylthio group, a butylthio group, a pentylthio group, etc. The lower alkyl group includes a methyl group, an ethyl group, a propyl group, a butyl group, an isopropyl group, a sec-butyl group, etc. The lower alkylamino group includes methylamino group, an ethylamino group, a propylamino group, a butylamino group, a pentylamino group, an isopropylamino group, a sec-butylamino group, a neopentylamino group, etc. The lower alkoxy group includes a methoxy group, an ethoxy group, a propoxy group, an isopropoxy group, a butoxy group, a tert-butoxy group, a pentyloxy group, etc. The substituents in the "lower alkyl group" are a hydroxy group or a phenyl group.

Suitable compounds of formula (I) are those wherein $R^1$ is a phenyl lower alkyl group, a lower alkanoyl group, an azido group, a lower alkylthio group or a lower alkanoyl amino group; $R^2$ is a hydrogen atom; $R^3$ is as defined above; and $R^4$ is a hydrogen atom or a hydroxy lower alkyl group.

Further compounds of formula (I) are those wherein $R^1$ and $R^2$ are a hydrogen atom; $R^3$ is as defined above; and $R^4$ is a lower alkyl group, a hydroxy lower alkyl group, or a group shown by formula —CH$_2$COA, wherein A is as defined above.

Still further compounds of formula (I) are those wherein $R^1$ is an azido group and $R^2$, $R^3$, and $R^4$ are as defined above.

Yet further compounds of formula (I) are those wherein $R^1$ and $R^2$ are a lower alkyl group and $R^3$ and $R^4$ are as defined above.

The compound (I) of the present invention has asymmetric carbon atoms in some cases and thus has stereoisomers based thereon. The desired compound of the present invention includes any separated isomer and any isomer mixture.

The compound (I) of the present invention may form a salt with a non-toxic acid (for example, an inorganic acid salt such as a hydrochloride, a sulfate, etc., and an organic acid salt such as a citrate, an acetate, a tartrate, etc.), and a salt with a non-toxic base (for example, a salt with an inorganic base such as a sodium salt, a potassium salt, etc., and a salt with an organic base such as a diethylamine salt, a trimethylamine salt, etc.)

A known compound related to the compounds of the present invention shown by formula (I) is L-pyroglutamyl-L-histidyl-L-prolinamide (pGlu-His-Pro-NH$_2$), called "Thyrotropin Releasing Hormone" (TRH).

The existence of TRH has been known since the 1960's but the structure thereof was confirmed in 1970 (Endocrinology, 86, 1143 (1970). TRH is said to be a hormone controlling the release of thyrotropin (TSH) in the hypophysis of a mammal. However, by investigations made since, it has been clarified that the biological function of the tripeptide TRH is not limited to control of the release of TSH, but is actions on the central nervous system (CNS), and a field of new investigations has been developed based on the discovery (Science, 178, 417 (1972) and Lancet, 2, 999 (1972)). Thus, it is known that TRH and the derivatives thereof act on the CNS, such as to decrease the duration of sleep caused by barbiturates or alcohol, control hypothermia induced by various medicaments, accelerate motor activity, prevent haloperidol-induced catalepsy, enhance memory, and to show anit-psychotic and anti-depressive effects, etc., in addition to the TSH releasing activity (U.S. Pat. Nos. 3,865,934 and 3,932,623). Furthermore, it has been discovered that TRH is useful for improving or treating functional or organic disturbances in the brain, for example, disturbance of consciousness caused by head injury, brain surgery, cerebro-vascular disorders, brain tumors, etc., in particular, acute or semiacute disturbance of consciousness (Belgian Pat. No. 839,833).

The development of TRH derivatives showing a weaker TSH releasing activity than TRH or almost no TSH releasing activity and having CNS activity the same as or higher than that of TRH would be desirable. Thus, various TRH derivatives were synthesized for the foregoing purpose and actions on the CNS have been further enlarged. As compounds synthesized for this purpose, there is known a TRH derivative which has a weaker TSH releasing activity than TRH, has a narcotic antagonizing action, an action of increasing spontaneous activity, or a dopamine-like action, and is said to be useful for the improvement or treatment of somnifacients poisoning, disturbance of consciousness, child hyperactivity schizophrenia, nervous depression, and Parkinson's disease (Japanese Patent Publication (unexamined) No. 116,465/'77) and a TRH derivative which acts to improve and treat the disturbance of consciousness after an external head injury and to decrease the continuation time of sleep by hexobarbital, and is said to be useful for the treatment of a patient having disturbance of consciousness caused by organic or functional disturbances in the brain, the treatment of a patient showing senility or mental fatigue, and the treatment of depression (Japanese Patent Publication (unexamined) No. 59,714/'81).

The compounds of the present invention have the characteristic that the pyroglutamyl (pGlu) structural moiety of TRH is replaced by an azetidinone structure ($\beta$-lactam structure).

As to medicinal action, the compounds of the present invention can have stronger CNS actions than TRH and conventionally known TRH derivatives and hence are useful as medicaments. For example, the compounds of the present invention can be useful for improving disturbance of consciousness in schizophrenia, nervous depression, the sequels to cerebro-vascular disorders, head injury, senile dementia, epilepsy, etc., or improving hypobulia, depressive syndrome, memory loss, etc.

The compounds of the present invention can be orally or parenterally administered alone or in pharmacologically acceptable carrier, excipient, diluent, etc., in the form of powders, granules, tablets, capsules, injections (intravenous, subcutaneous, or intramuscular injections), or suppositories. The dose of the compound of the present invention differs according to the particular compound, the age, weight and symptom of the patient, the manner of administration, etc., but is usually 0.001 to 10 mg, preferably 0.01 to 0.1 mg (one dose) in the case of injection and 0.05 to 500 mg, preferably 0.1 to 10 mg (one dose) in the case of oral administration.

The following experiments show the action on low body temperature induced by pentobarbital (Experiment 1), and on acute toxicity for typical compounds of the present invention.

EXPERIMENT 1

Pentobarbital-induced hypothermia

Nine male mice weighing 18 to 22 g were used for each dosage of the test compounds. Mice were given intravenously various doses of test compounds 10 minutes after pentobarbital (55 mg/kg i.p.). Rectal temperature was measured before pentobarbital dosing and immediately before and 30 minutes after the test compounds. Effects of test compounds were evaluated as $ED_{1.5°\ C.}$, the dose required to reduce by 1.5° C. pentobarbital-hypothermia of control group of mice which received only pentobarbital and saline. The results are shown in Talbe 1.

TABLE 1

| Test Compound | (A) |
|---|---|
| $N^\alpha$—[(S)—1-Hydroxymethyl-4-oxo-2-azetidinyl-carbonyl]-L-histidyl-L-prolinamide | 0.04 |
| $N^\alpha$—[(3S,4S)—3-(1-Hydroxyethyl-4-oxo-2-azetidinyl-carbonyl]-L-histidyl-L-prolinamide | 0.07 |
| $N^\alpha$—[(2S,3R)—3-Benzyl-4-oxo-2-azetidinyl-carbonyl]-L-histidyl-L-prolinamide | 0.04 |
| $N^\alpha$—[(2S,3R)—3-Azido-4-oxo-2-azetidinyl-carbonyl]-L-histidyl-L-prolinamide | 0.01> |
| $N^\alpha$—[(2R,3R)—3-Methylthio-4-oxo-2-azetidinyl-carbonyl]-L-histidyl-L-prolinamide | 0.08 |
| $\tau$-Methyl-$N^\alpha$—[(2S,3R)—3-methyl-4-oxo-2-azetidinyl-carbonyl]-L-histidyl-L-prolinamide | 0.02 |
| $N^\alpha$—[(S)—3,3-Dimethyl-4-oxo-2-azetidinylcarbonyl]-$\tau$-methyl-L-histidyl-L-prolinamide | 0.01 |
| TRH | 0.1 |

(A) Reversal effect against pentobarbital-hypothermia $ED_{1.5°\ C.}$ (mg/kg i.v.)

Acute toxicity

An aqueous physiological saline solution of 800 mg/kg of a test compound, $N^\alpha$-[(S)-3,3-dimethyl-4-oxo-2-azetidinylcarbonyl]-L-histidyl-L-prolinamide, was intravenously administered to one group of nine male mice and they were observed for 24 hours but no deaths were observed. That is, $LD_{50}$ (i.v.) of the compound of the present invention was higher than 800 mg/kg. On the other hand, $LD_{50}$ (i.v.) was 751 mg/kg (i.v.) in the case of administering TRH to mice.

According to the present invention, the desired compounds can be produced by the reaction courses shown by the following schemes.

Process 1:

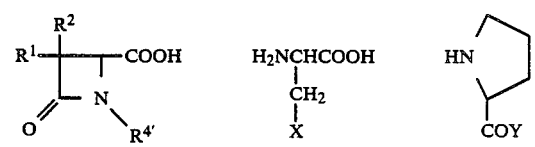

Process 1:

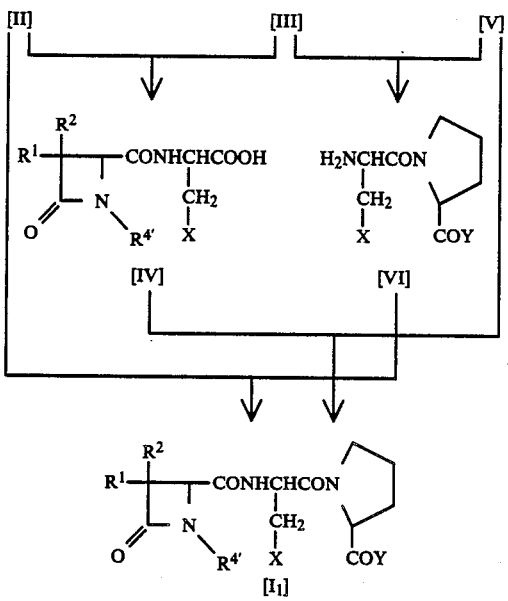

The compound [I₁] can be converted into (I₂) by hydrolysis when Y is an alkoxy group or, by reaction with an amine when Y is a hydroxy group.

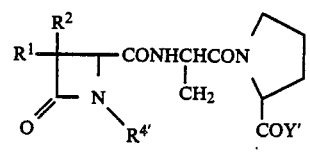

wherein $R^1$, $R^2$, $R^3$ and Y are as defined above; $R^{4'}$ represents a hydrogen atom or a substituted or unsubstituted lower alkyl group; and $Y'$ represents a hydroxy group, an amino group or a mono- or di-lower alkylamino group.

Namely, according to this process, the desired compound of formula (I) can be produced:

(a) by reacting compounds of formula (II) and formula (III) to form a compound of formula (IV) and then reacting the compound of formula (IV) and a compound of formula (V); or, (b) by reacting compounds of formula (III) and formula (V) to form a compound of formula (VI) and then reacting the compound of formula (VI) thus obtained with a compound of formula (II).

Also, the thus obtained compound of formula (I₁) can be converted into a compound of formula (I₂) by converting the substituent Y.

Process 2:

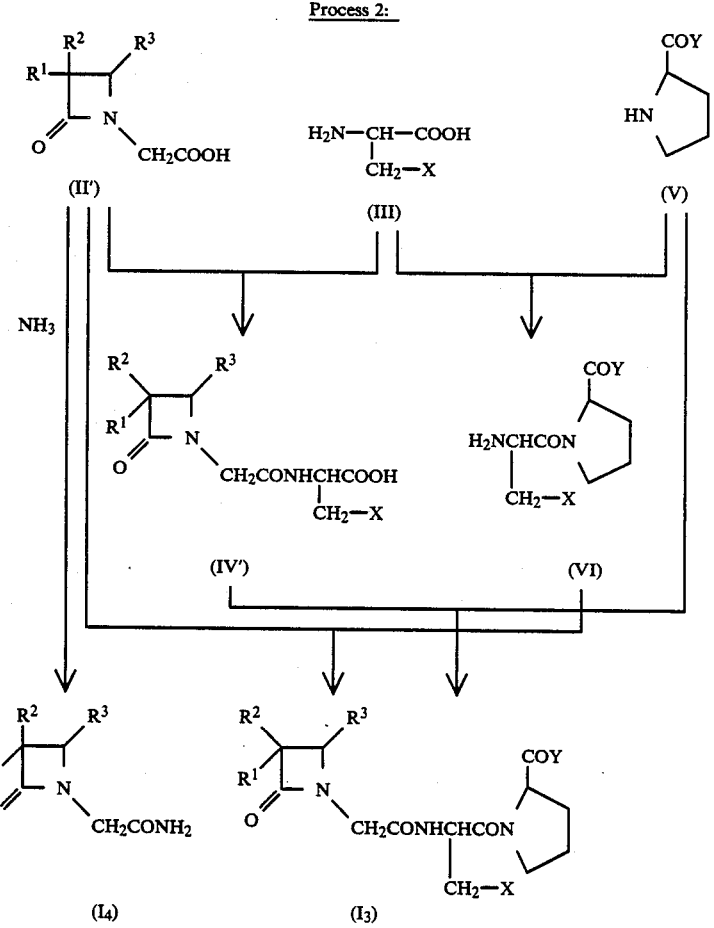

wherein $R^1$, $R^2$, $R^3$, X and Y are as defined above.

Thus according to this process, a compound of formula (I₃) can be produced:

(a) by reacting compounds of formula (II') and formula (III) to form a compound of formula (IV') and then reacting the compound of formula (IV') and a compound of formula (V); or, (b) by reacting compounds of formula (III) and formula (V) to form a compound of formula (VI) and then reacting the compound of formula (VI) thus obtained with a compound of formula (II'); or, (c) by treating the compound of formula (II') with ammonia.

The production reaction for compounds of formula (I₁), (I₂) or (I₃) employed in the foregoing process (a) or (b) is a peptide synthesis reaction and can be performed in a conventional manner, e.g., using dicyclohexylcarbodiimide as a condensing agent, an azide method, an acid chloride method, an acid anhydride method, or an active ester method, etc. To conduct these methods, the functional groups of the raw material compound, such as an amino group, an imino group, a carboxy group, etc., which do not take part in the reaction, are usually protected prior to the performance of the peptide forming reaction in each step. Further, an amino group, an imino group, or a carboxy group of the compound, which takes part in the reaction, is, if necessary and desired, activated.

Furthermore, for converting the desired compound of formula (I₁) into other desired compound of the present invention by converting the substituent Y of the compound of formula (I₁), the reaction conditions may be suitably selected depending upon the properties of the compounds taking part in the reaction.

Examples of the protective group for the amino group are a benzyloxycarbonyl group, a tert-butoxycarbonyl group, a p-methoxybenzyloxycarbonyl group, a phthaloyl group, a trifluoroacetyl group, etc., and examples of the protective group for the imino group are a tosyl group, a benzyloxycarbonyl group, a p-methoxybenzyloxycarbonyl group, a benzyl group, a 2,4-dinitrophenyl group, etc.

Examples of the protective group for the carboxy group include a form of an ester such as a methyl ester, an ethyl ester, a benzyl ester, a p-nitrobenzylester, tert-butyl ester, etc.

The activation of the group which takes part in the reaction is, for example, by a phosphazo process using phosphorus trichloride, an isocyanate process using phosgene, or a phosphorous acid ester process when the group is an amino group or an imino group, or, by formation of an active ester (2,4-dinitrophenol ester, N-hydroxysuccinimide ester, etc.), an azide group or a carboxylic anhydride, when the group is a carboxy group.

Among the foregoing methods of performing the peptide synthesis reaction, it is preferred to perform the reactions of the compound of formula (IV) and the compound of formula (V) by the process using dicyclohexyl carbodiimide as the condensing agent, the active ester process or the azide process. Also, a process of directly forming a peptide using the N-carboxy anhydride without using any protective group may be employed.

Next, the peptide forming reaction can be performed in an inert solvent at room temperature or with heating in a conventional manner. Examples of suitable solvents are dimethylformamide (DMF), ethyl acetate, dichloromethane (methylene chloride), tetrahydrofuran, etc.

If it is necessary to remove a protective group from the reaction product, the protective group can easily be removed by catalytic reduction when the protective group is a benzyl group; by catalytic reduction or treatment with hydrobromic acid-acetic acid when it is benzyloxycarbonyl or p-methoxybenzyloxycarbonyl group; or, by acid decomposition when the protective group is a tert-butoxycarbonyl group.

Further, the reaction for producing the compound of formula (I₄) employed in the foregoing (c) is an amide synthesis reaction and can be performed in a conventional manner. Techniques which can be usually employed include a dehydration process using an excess of ammonia in the presence of active alumina as a catalyst, an acid halide process, an acid anhydride process or an ester ammonolysis process. In particular, the ester ammonolysis process is advantageous, taking easy access to raw materials, yield, etc., into account.

The reaction is performed treating the compound of formula (II') with an excess of liquid ammonia, preferably a mixture of water or glycol, which is known to promote the reaction, and ammonia, under cooling or at room temperature, in an organic solvent such as methanol, ethanol, etc. For purpose of promoting the reaction, ammonium chloride, sodium methoxide, sodium amide, butyl lithium, etc. may be employed as a catalyst.

The present invention will be further explained by referring to the examples.

The processes for producing the raw materials used in the examples are illustrated as reference examples.

The abbreviations employed in the examples and reference examples have the following meanings:

NMR: Nuclear magnetic resonance spectrum
IR: Infrared absorption spectrum
Mass: Mass analysis spectrum
His: Histidine
Pro: Proline
TsOH: p-Toluenesulfonic acid
DCC: Dicyclohexylcarbodiimide
DMF: Dimethylformamide
HOBT: 1-Hydroxy-1,2,3-benzotriazole
THF: Tetrahydrofuran
Ph: Phenyl group
t-Bu: t-Butyl group

REFERENCE EXAMPLE 1

(Raw Material of Example 1)

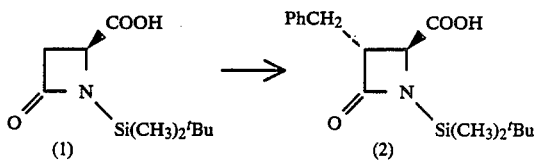

In 6 ml of THF was dissolved 836.3 mg of diisopropylamine and the solution was cooled to 0° C. in a nitrogen atmosphere. To the solution was gradually added 5.2 ml of a n-hexane solution containing 530 mg of n-butyl lithium at 0° C. The mixture was stirred for 10 minutes at the same temperature. Then, a solution of 920 mg of (S)-1-t-butyldimethylsilyl-4-oxo-2-azetidinecarboxylic acid (1) in 8 ml of dry THF was added to the mixture at 0° C. followed by stirring at room temperature for 30 minutes. The solution was cooled to 0° C. and 820.8 mg of benzyl bromide was added to the solution. The mixture was then stirred at room temperature for 30 minutes. The solution was again cooled to 0° C. and a 10% citric acid solution was added thereto to render acidic. Ether was added to the mixture to separate from the aqueous phase. After the ethereal phase was dried, the solvent was removed by distillation to obtain 858 mg of (2S,3R)-1-t-butyldimethylsilyl-3-benzyl-4-oxo-2-azetidinecarboxylic acid (2) showing a melting point of 99°~102° C. as colorless crystals.

NMR (CDCl$_3$) δppm: 0.00 (3H, s, Si—CH$_3$), 0.20 (3H, s, Si—CH$_3$), 0.76 (9H, s, t—Bu), 2.80~3.30 (2H, m, PhC$\underline{H}_2$), 3.40~3.72 (1H, m,

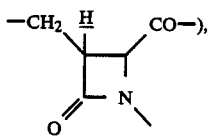

3.98 (1H, d,

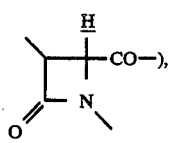

7.28 (5H, s, Ph), 10.05 (1H, OH)
IR (KBr) cm$^{-1}$: 3000, 2910, 2840, 2610, 2480, 1730, 1680

EXAMPLE 1

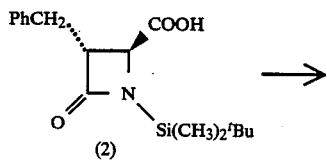

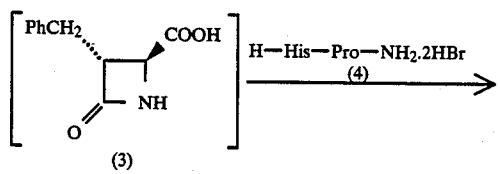

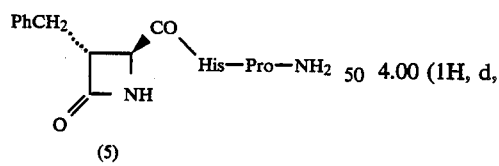

To a solution of 858.2 mg of compound (2) in 16 ml of methanol was added 4.0 ml of 1N-hydrochloric acid at 0° C. followed by stirring at room temperature for 1.75 hours. The reaction mixture was cooled to 0° C. and 4.0 ml of 1N-sodium hydroxide was added thereto. The solvent was removed by distillation under reduced pressure and the residue was dried by azeotropic distillation with acetonitrile-benzene.

The thus obtained (2S,3R)-3-benzyl-4-oxo-2-azetidine-carboxylic acid (3) was dissolved in 14 ml of dry DMF without purifying it. To the solution were added 472 mg of HOBT and 610 mg of DCC at 0° C. and the resulting mixture was stirred at the same temperature for 15 minutes (Reaction mixture A).

In 18 ml of dry DMF was dissolved 1.11 g of L-histidyl-L-prolinamide dihydrobromide (4) and 0.749 ml of triethylamine was added to the solution at −10° C. After stirring at the same temperature for 30 minutes, the precipitated crystals were filtered off under cooling to obtain a clear filtrate (Reaction mixture B).

Mixture B was added to mixture A. After stirring the mixture at 0°~5° C. overnight, the stirring was continued for further 3 hours at room temperature. After the precipitated crystals were filtered, the filtrate was concentrated under reduced pressure and the residue was subjected to column chromatography using 150 ml of silica gel and eluted with chloroform-methanol-conc. ammonia water (40:10:1) to obtain a crude product. The crude product was subjected to column chromatography using 100 ml of silica gel and eluted with ethyl acetate-methanol (2:1) to obtain 351 mg of N$^\alpha$-[(2S,3R)-3-benzyl-4-oxo-2-azetidinylcarbonyl]-L-histidyl-L-prolinamide (5).

NMR (D$_2$O) δppm: 1.70~2.40 (4H, m,

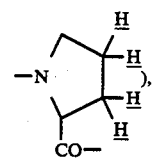

2.80~3.20 (4H, m,

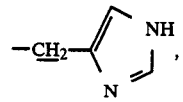

pHC$\underline{H}_2$), 3.20~3.80 (3H, m,

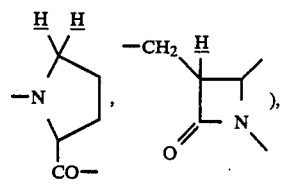

4.00 (1H, d,

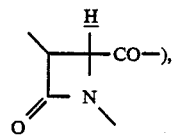

3.24~3.48 (1H, m, CH), 5.10 (1H, t, CH), 6.97 (1H,

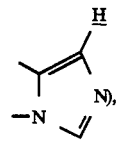

7.36 (5H, s, Ph), 7.68 (1H,

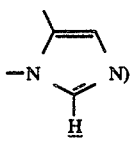

IR (KBr) cm⁻¹: 3250 (broad), 1750, 1665, 1635, 1520, 1440

Mass (m/z) FAB: 439 (M+1), 396, 325, 297, 280

EXAMPLE 2

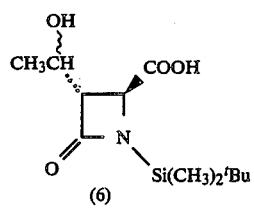

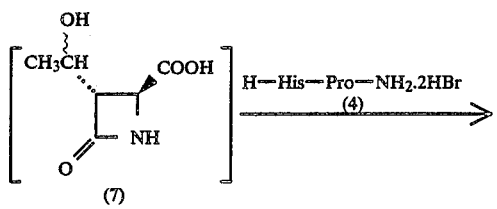

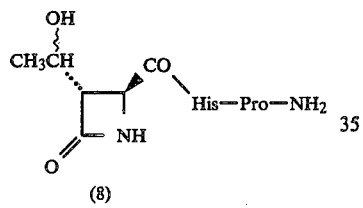

A solution of 822 mg of (2S,3S)-1-butyldimethylsilyl-3-(1-hydroxyethyl)-4-oxo-2-azetidinecarboxylic acid (6) in 18 ml of methanol was cooled to 0° C. and 4.5 ml of 1N-hydrochloric acid was dropwise added to the solution. The mixture was stirred at room temperature for 2.5 hours. The reaction mixture was cooled to 0° C. and 4.5 ml of 1N-sodium hydroxide was added thereto. After the solvent was removed by distillation at room temperature under reduced pressure, the residue was dried by azeotropic distillation with acetonitrilebenzene. The resulting (2S,3S)-3-(1-hydroxyethyl)-4-oxo-2-azetidinecarboxylic acid (7) was dissolved in 15 ml of dry DMF without purifying it. To the solution were added 527 mg of HOBT and 680 mg of DCC at 0° C. followed by stirring for 15 minutes at the same temperature (Reaction mixture A).

In 20 ml of dry DMF was dissolved 1.239 g of L-histidyl-L-prolinamide dihydrobromide (4). After the solution was cooled to 10° C., 0.835 ml of triethylamine was added thereto. The mixture was stirred at the same temperature for 30 minutes and then cooled. The precipitated crystals were filtered off to obtain the filtrate (Reaction mixture B).

Mixture B was added to mixture A. After stirring the mixture at 0°~5° C. overnight, the stirring was continued for further 3 hours at room temperature. After the precipitated crystals were filtered, the filtrate was concentrated under reduced pressure. The residue was purified by column chromatography using 200 ml of silica gel (Wakogel C-200) and ethyl acetate-methanol-conc. ammonia water (60:30:3) as eluent to obtain 310 mg of Nα-[(2S,3S)-3-(1-hydroxyethyl)-4-oxo-2-azetidinylcarbonyl]-L-histidyl-L-prolinamide (8).

NMR (D₂O) δppm: 1.23 (d, methyl), 1.30 (d, methyl), 3H in combination of both; 1.60~2.40 (4H, m,

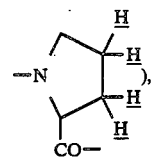

2.90~3.30 (3H, m), 3.30~4.00 (2H, m), 4.11 (1H, d,

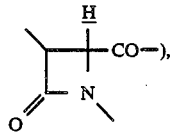

4.20 (1H, m,

4.40 (1H, m, CH), 4.98 (1H, m, CH), 7.04 (1H, s,

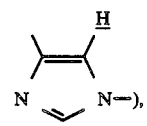

7.76 (1H, s,

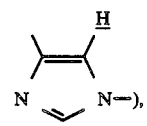

IR (KBr) cm⁻¹: 3250 (broad), 2960, 2850, 1740, 1660, 1630, 1530, 1440

Mass (m/z) FD: 392 (M+)

REFERENCE EXAMPLE 2

(Raw Material of Example 3)

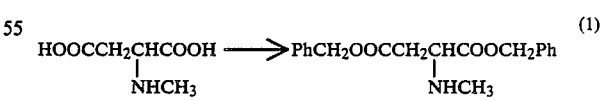

L-N-Methylaspartic acid (9), 2.0 g, 13.6 ml of benzyl alcohol and 3.1 g of p-toluenesulfonic acid monohydrate were mixed with 90 ml of benzene and the resulting mixture was heated under reflux for 4 hours in a flask equipped with a Dean-Stark apparatus. After cooling, 50 ml of ether was added to the mixture, a saturated sodium bicarbonate aqueous solution was added thereto to render basic and the organic layer was separated.

After the organic layer was washed with a saturated sodium chloride aqueous solution and dried, the solvent was removed by distillation under reduced pressure. The residue was purified by subjecting to column chromatography using 300 ml of silica gel (Wakogel C-200) and a solvent mixture of ethyl acetate-benzene (1:1) as an eluant to obtain 2.53 g of dibenzyl L-N-methylaspartate (10).

NMR (CDCl$_3$) δppm: 1.77 (1H, s, NH), 2.40 (3H, s, N—CH$_3$), 2,60~2.90 (2H,

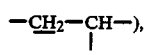

3.50~3.80 (1H,

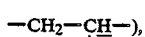

5.09 (2H, s, PhCH$_2$), 5.14 (2H, s, PhCH$_2$), 7.36 (10H, s, Ph)

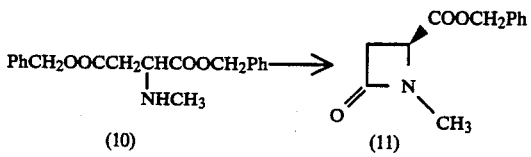

In 20 ml of dry ether was dissolved 1.73 g of compound (10) and 6.4 ml of a 0.828 mol solution of t-butyl magnesium chloride was gradually added to the solution at −10° to 0° C. under an atmosphere of nitrogen. After stirring for 1 hour at the same temperature, the reaction mixture was allowed to stand at room temperature overnight. Dry THF, 10 ml, was added to the reaction mixture. After stirring at room temperature for 1 hour, the reaction mixture was cooled to 0° C. and 10.6 ml of 1N-hydrochloric acid was added thereto to separate the organic layer. The aqueous layer was extracted twice with 10 ml of ether. The organic layers were combined and washed with a saturated sodium chloride aqueous solution. After drying, the solvent was removed by distillation under reduced pressure. The residue was subjected to column chromatography using 50 ml of silica gel (Wakogel C-200). Elution with ethyl acetate-n-hexane (1:1) gave 155.3 mg of (S)-benzyl 1-methyl-4-oxo-2-azetidinecarboxylate (11) as a yellow oil.

NMR (CDCl$_3$) δppm: 2.87 (3H, s, N—CH$_3$), 2.94 (1H, d, d,

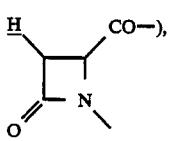

3.27 (1H, d, d,

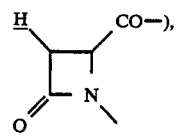

4.08 (1H, d, d,

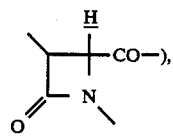

5.21 (2H, s, PhCH$_2$), 7.38 (5H, s, Ph)
IR (CHCl$_3$) cm$^{-1}$: 1745

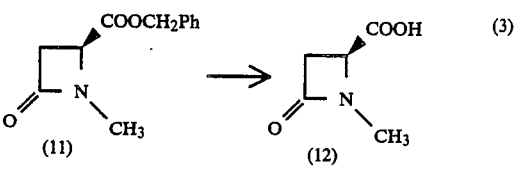

In 10 ml of methanol was dissolved 450 mg of compound (11) and 45 mg of 10% Pd-C was added to the solution followed by catalytic hydrogenation at ambient temperature under an atmospheric pressure of hydrogen. The catalyst was filtered off and the solvent was removed by distillation under reduced pressure to obtain 258 mg of (S)-1-methyl-4-oxo-2-azetidinecarboxylic acid (12).

NMR (CD$_3$OD) δppm: 2.94 (3H, s, N—CH$_3$), 4.17 (1H, d, d,

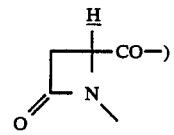

EXAMPLE 3

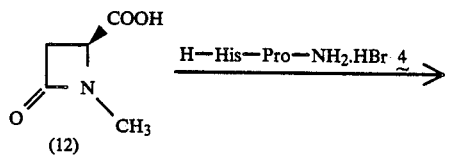

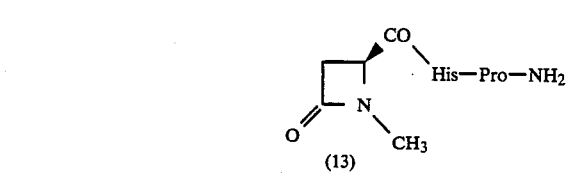

In 25 ml of dry DMF was suspended 826 mg of L-histidyl-L-prolinamide dihydrobromide (4) and 0.557 ml of triethylamine was dropwise added slowly to the suspension at −15° to −10° C. After stirring the mixture at the same temperature for 30 minutes, insoluble materials were filtered off under cooling to obtain a clear filtrate. To the filtrate were added 258 mg of compound (12), 351 mg of HOBT and 453 mg of DCC at −10° C. After stirring the mixture at −10° to 0° C. for 2 hours, the mixture was allowed to stand in a refrigerator for 2 days. After the precipitated insoluble matters were filtered off, the solvent was removed by distillation under reduced pressure. The resulting residue was subjected to column chromatography using 150 ml of silica gel (Wakogel C-200). By eluting with chloroform-methanol-conc. ammonia water (40:10:1), 352.6 mg of $N^\alpha$-[(S)-1-methyl-4-oxo-2-azetidinylcarbonyl]-L-histidyl-L-prolinamide (13) was obtained.

NMR (D₂O) δppm: 1.70~2.50 (4H, m,

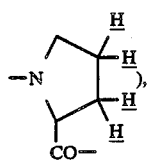
), 2.75 (3H, s, N—CH₃), 2.80~3.40 (4H, m,

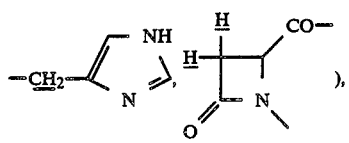
), 3.40~4.00 (2H, m,

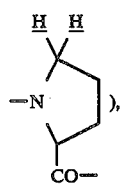
), 4.22 (1H, d, d,

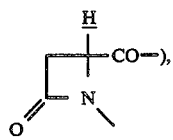
), 4.43 (1H, m, CH), 5.00 (1H, t, CH), 7.07 (1H,

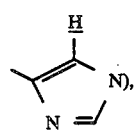
), 7.74 (1H,

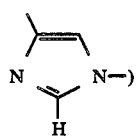
)

IR (KBr) cm⁻¹: 3250 (broad), 2960, 2870, 1735, 1665, 1680
Mass (m/z) FAB: 363 (M⁺+1)

REFERENCE EXAMPLE 3
(Raw Material of Example 4)

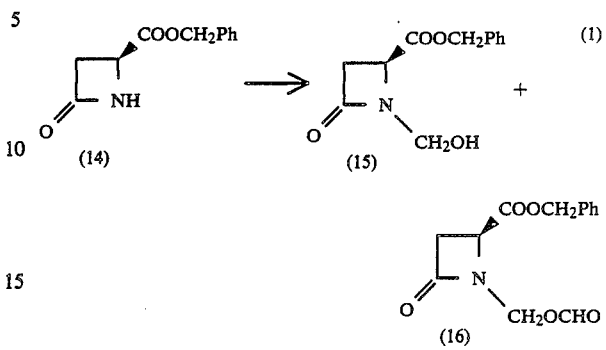

To a mixture of 10 ml of formic acid and 20 ml of formalin was added 3 g of (S)-benzyl 4-oxo-2-azetidinecarboxylate (14). The resulting mixture was kept at 50° C. for 15 minutes. After cooling, the mixture was made alkaline with a saturated sodium bicarbonate aqueous solution and extracted twice with 50 ml of ether. The ethereal extracts were washed with a saturated sodium chloride aqueous solution and then dried. The solvent was removed by distillation under reduced pressure and the residue thus obtained was purified by column chromatography using silica gel. Thus, 970 mg of (S)-benzyl 1-hydroxymethyl-4-oxo-2-azetidinecarboxylate (15) and 1.78 g of (S)-benzyl 1-formyloxymethyl-4-oxo-2-azetidinecarboxylate (16) were obtained.

Physical Properties of Compound (15)

NMR (CDCl₃) δppm: 3.00 (1H, d, d,

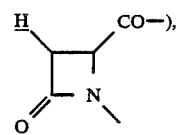
), 3.26 (1H, d, d

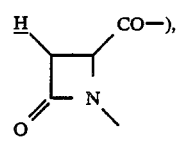
), 4.34 (1H, d, d,

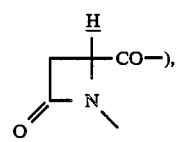
), 4.72 (2H, q, —CH₂OH), 5.19 (2H, s, PhCH₂), 7.32 (5H, s, Ph)
IR (CHCl₃) cm⁻¹: 1760, 1740 (shoulder)

Physical Properties of Compound (16):

NMR (CDCl₃) δppm: 3.00 (1H, d, d, 3.29 (1H, d, d,

[structure: azetidinone with H and CO—]

4.32 (1H, d, d,

[structure: azetidinone with H and CO—]

5.20 (2H, s, PhCH₂), 5.26 (1H, q, —N—CH₂—), 7.32 (5H, s, Ph), 7.96 (1H, s, —CHO)

IR (CHCl₃) cm⁻¹: 1775, 1722

[reaction scheme: (16) COOCH₂Ph azetidinone with N-CH₂OCHO → (17) COOH azetidinone with N-CH₂OCHO] (2)

In 20 ml of methanol was dissolved 1.05 g of compound (16) and 100 mg of 10% Pd-C was added to the solution followed by catalytic hydrogenation at ambient temperature under atmospheric pressure of hydrogen. The catalyst was filtered off and the solvent was removed by distillation under reduced pressure to obtain 650 mg of (S)-1-formyloxymethyl-4-oxo-2-azetidinecarboxylic acid (17).

NMR (DMSO-d⁶) δppm: 2.92 (1H, d, d,

[structure]

3.31 (1H, d, d,

[structure]

4.20 (1H, d, d,

[structure]

5.20 (2H, q, —N—CH₂), 8.21 (1H, s, —CHO)

EXAMPLE 4

[reaction scheme: (17) COOH azetidinone with N-CH₂OCHO + H—His—Pro—NH₂·2HBr (4) → (18) CO—His—Pro—NH₂ azetidinone with N-CH₂OH]

In 26 ml of dry DMF was suspended 1.569 g of compound (4) and 1.187 ml of triethylamine was dropwise added slowly to the suspension at −15° to −10° C. After stirring the mixture at the same temperature for 30 minutes, insoluble matters were filtered off under cooling to obtain a clear filtrate. The filtrate was cooled to −10° C. and, a solution of 657.8 mg of compound (17) and 667 mg of HOBT in 20 ml of dry DMF was dropwise added gradually to the filtrate. Then, 861 mg of DCC was added thereto. After stirring the mixture for 2 hours at −10° to 0° C., the mixture was allowed to stand overnight in a refrigerator. The temperature was elevated to room temperature again and the precipitated crystals were filtered off. The solvent of the filtrate was removed by distillation under reduced pressure and the thus obtained residue was purified by column chromatography using 200 ml of silica gel (Wakogel C-200). By eluting with ethyl acetate-methanol-conc. ammonia water (60:30:3), 840 mg of Nα-[(S)-1-hydroxymethyl-4-oxo-2-azetidinylcarbonyl]-L-histidyl-L-prolinamide (18) was obtained.

NMR (D₂O) δppm: 1.60∼2.50 (4H, m,

[structure: pyrrolidine ring]

2.6∼4.00 (6H, m,

[structure: azetidinone with H, H and CO—]

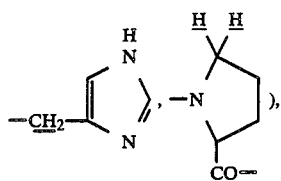

4.64 (2H, q, N—CH₂—O—), 5.00 (1H, t, CH), 7.07 (1H,

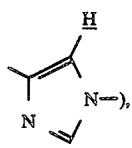

7.76 (1H,

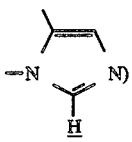

IR (KBr) cm⁻¹: 3250 (broad), 2950, 2860, 1745, 1665, 1630

Mass (m/z) FAB: 363 (M⁺+1)

REFERENCE EXAMPLE 4

(Raw Material of Example 5)

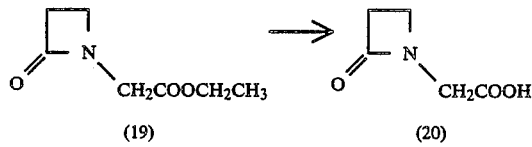

In 28 ml of methanol was dissolved 1.44 g of ethyl α-(2-oxo-1-azetidinyl)acetate (19) and 10 ml of a 1N sodium hydroxide aqueous solution was dropwise added to the solution under ice cooling. The mixture was reacted at 10° to 15° C. for 1 hour. The reaction solution was ice-cooled and 10 ml of 1N-hydrochloric acid was added thereto. Methanol was removed by distillation under reduced pressure. After the remaining aqueous solution was saturated with sodium chloride, the mixture was extracted 3 times with 140 ml of ethyl acetate. The ethyl acetate extracts were combined and dried over anhydrous sodium sulfate and then concentrated to obtain 950 mg of α-(2-oxo-1-azetidinyl)acetic acid (20).

NMR (CDCl₃+CD₃OD) δppm: 3.97 (2H, s), 3.45 (2H, t, J=4 Hz), 3.02 (2H, t, J=4 Hz)

IR (CHCl₃ solution) cm⁻¹: 1740

Mass (m/z): 129 (M⁺)

EXAMPLE 5

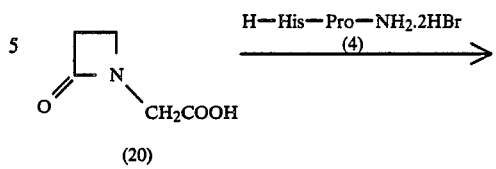

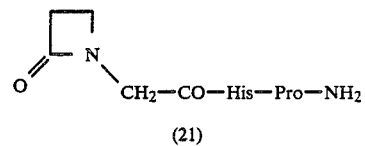

In 27 ml of DMF was dissolved 2.18 g of L-histidyl-L-prolinamide dihydrobromide (4). The solution was cooled to −15° to −10° C. and 1.63 ml of triethylamine was added thereto. After reacting at this temperature for 20 minutes, the formed precipitates were filtered off to obtain a solution of L-histidyl-L-prolinamide. The solution was immediately used for the following synthesis. In a mixture of 14 ml of DMF and 14 ml of methylene chloride were dissolved 868 mg of compound (20) and 859 mg of HOBT and, 1.31 g of DCC was added to the solution under ice cooling. The mixture was reacted for 40 minutes. To the reaction mixture was added the foregoing DMF solution of L-histidyl-L-prolinamide. The reaction was performed at 0° to 4° C. overnight. The precipitates were filtered off and the filtrate was concentrated to dryness. The residue was subjected to column chromatography using silica gel. By eluting with chloroform-methanol-conc. ammonia water (80:20:2), 610 mg of Nα-(2-oxo-1-azetidinylacetyl)-L-histidyl-L-prolinamide (21) was obtained.

NMR (CD₃OD) δppm: 760 (1H), 6,98 (1H), 4.44 (1H, m), 3.91 (2H, s), 3.74 (1H, m), 2.9~3.1 (4H, m), 1.8~2.2 (4H, m)

IR (KBr) cm⁻¹: 3360, 1730, 1665, 1630

Mass (m/z): 362 (M⁺)

EXAMPLE 6

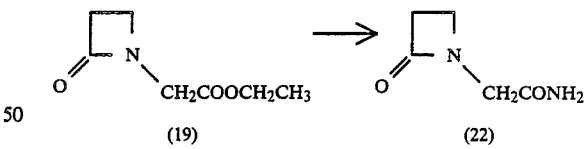

In 0.8 ml of methanol was dissolved 843 mg of compound (19) and 0.4 ml of conc. ammonia water was added to the solution under ice cooling followed by stirring at room temperature for 18 hours. The reaction mixture was concentrated under reduced pressure. The residue was purified by column chromatography (30 g of silica gel, chloroform-methanol=10:1) to obtain 550 mg of a roughly purified product. The product was treated with a solvent mixture of 3 ml of chloroform and 3 ml of ether to crystallize. Thus 360 mg of α-(2-oxo-1-azetidinyl)acetamide (22) was obtained as colorless crystals.

m.p. 112°~113° C.

NMR (CDCl₃) δppm: 3.04 (2H, t, J=4 Hz), 3,42 (2H, t, J=4 Hz), 3.90 (2H, s), 5.88 (1H, broad), 6.35 (1H, broad)

REFERENCE EXAMPLE 5

(Raw Material of Example 7)

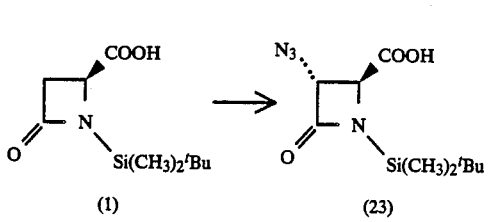

(1)  (23)

In 30 ml of dry THF was dissolved 3.4 g of (S)-1-t-butyldimethylsilyl-4-oxo-2-azetidinecarboxylic acid (1) and the solution was added to a solution of 30.6 mmols of lithium diisopropylamide in 22 ml of dry THF at 0° C. A cooling bath was removed and the mixture was stirred for 35 minutes. Thereafter, the mixture was cooled to −70° C. and a solution of 3.5 g of p-toluenesulfonylazide in 18 ml of THF was dropwise added thereto. The mixture was stirred for 1 hour at −50° C. and again cooled to −70° C.

After 4.81 g of trimethylsilyl chloride was added to the mixture, the mixture was warmed to 40° C. followed by stirring for 6 hours. The reaction mixture was concentrated under reduced pressure and a solution of 3.7 g of hydrogen sodium carbonate in 100 ml of water was added to the residue. A 10% aqueous citric acid solution was added to the solution to adjust pH to 3. The aqueous solution was extracted with ether 3 times. The ethereal layers were combined and dried over anhydrous sodium sulfate. After filtering, the filtrate was concentrated to obtain 3.2 g of an oil. It was subjected to column chromatography using 100 g of silica gel. Elution with n-hexane-ethyl acetate (4:1) and (2:1) gave 1.6 g of (2S,3R)-1-t-butyldimethylsilyl-3-azido-4-oxo-2-azetidinecarboxylic acid (23) as a colorless solid.

(i) NMR (CDCl$_3$) δppm: 0.18 (3H, s, CH$_3$), 0.32 (3H, s, CH$_3$), 0.98 (9H, s, t-Bu), 4.00 (1H, d, J=3 Hz), 4.71 (1H, d, J=3 Hz)

(ii) IR (KBr) cm$^{-1}$: 2095, 1740, 1700

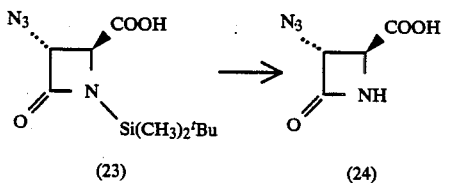

(23)  (24)

In 39 ml of methanol was dissolved 1.78 g of compound (23) and 9.85 ml of 1N hydrochloric acid was added to the solution. The mixture was stirred for 1.75 hours at room temperature. The reaction mixture was cooled to 0° C. and 9.85 ml of 1N sodium hydroxide was added thereto. The mixture was concentrated to dryness under reduced pressure to obtain an oil. The oil was dissolved in 10 ml of DMF and 3A molecular sieve was added thereto. After the mixture was allowed to stand overnight, the solvent was removed by distillation under reduced pressure to obtain (2S,3R)-3-azido-4-oxo-2-azetidinecarboxylic acid (24). This compound was used in the following Example 7 as it was.

EXAMPLE 7

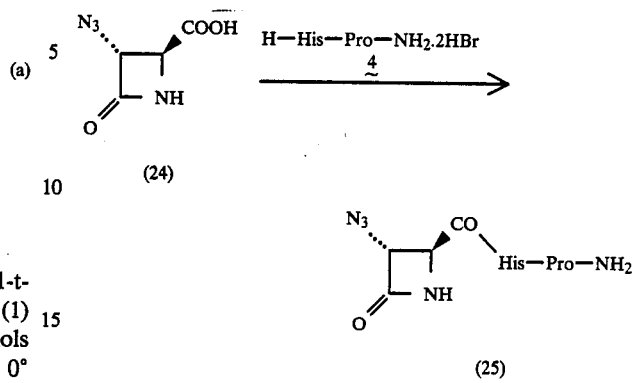

In a mixture of 15 ml of DMF and 15 ml of methylene chloride was dissolved compound (24) obtained in Reference Example 5(b) and 1.06 g of HOBT was added to the solution followed by ice cooling. After 1.62 g of DCC was added to the mixtures, the mixture was stirred at 0° C. for 40 minutes (reaction solution A).

On the other hand, 2.71 g of L-histidyl-L-prolinamide dihydrobromide (4) was dissolved in 32 ml of DMF and 2 ml of triethylamine was added to the solution at −15° C. The mixture was stirred at −5° C. for 20 minutes and the precipitated salt was filtered off to obtain a DMF solution of the free base (reaction solution B). Reaction solution B was added to reaction solution A. The mixture was stirred at 0° to 5° C. for 20 hours. After removing the insoluble matters by filtration, the filtrate was concentrated under reduced pressure. The thus obtained oil was subjected to column chromatography using 180 g of silica gel.

By eluting with chloroform-methanol-ammonia water (80:20:2), N$^\alpha$-[(2S,3R)-3-azido-4-oxo-2-azetidinylcarbonyl]-L-histidyl-L-prolinamide (25) was obtained. The product was lyophilized to obtain 58 mg as a colorless solid.

(i) NMR (d$^6$-DMSO) δppm: 1.86 (4H, m), 2.85~3.00 (2H, m), 4.08 (1H, d, J=2 Hz), 4.6~4.8 (2H, m), 6.96 (1H, s), 7.00 (1H), 7.58 (1H, s), 8.06 (1H), 8.65 (1H, d, J=8 Hz), 8.78 (1H)

(ii) IR (KBr) cm$^{-1}$: 3400, 2110, 1765, 1620~1680 (broad)

(iii) Mass (m/z) FAB: 390 (M+1), 362, 307

REFERENCE EXAMPLE 6

(Raw Material of Example 8)

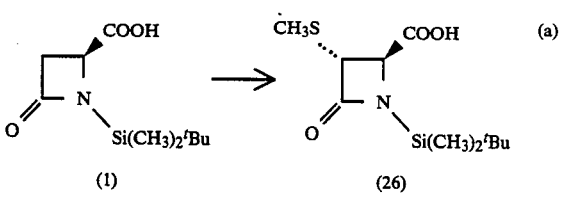

(1)  (26)

In 8 ml of dry THF was dissolved 920 mg of compound (1). The solution was added to a solution of 8.28 mmols of lithium diisopropylamide in 6 ml of THF at 0° C. Then, a cooling bath was removed and the solution was stirred for 35 minutes. Thereafter, the mixture was cooled to −70° C.

To the reaction mixture was added 0.47 ml of dimethyl disulfide and the mixture was stirred at −70° to −60° C. for 30 minutes and then at −50° C. for 1 hour. The cooling bath was removed and stirring was continued. When the temperature reached 0° C., the reaction mixture was poured into a mixture of 5 ml of a 10% citric acid aqueous solution, 30 ml of ice water and 50 ml of ether. The pH was adjusted to 3 to 4 with a 10% aqueous citric acid solution to separate the aqueous layer from the organic layer. The aqueous layer was extracted with 30 ml of ether and the extract was combined with the organic layer followed by washing with water. After drying over anhydrous magnesium sulfate, the solvent was removed under reduced pressure to obtain a pale yellow oil.

The oil was purified by column chromatography using 80 g of silica gel. By eluting with n-hexane-ethyl acetate (4:1), 272 mg of (2R,3R)-1-t-butyldimethylsilyl-3-methylthio-4-oxo-2-azetidinecarboxylic acid (26) was obtained as a white solid.

(i) NMR (CDCl$_3$) δppm: 0.16 (3H, s, CH$_3$), 0.32 (3H, s, CH$_3$), 0.97 (9H, s), 2.19 (3H, s, SCH$_3$), 4.00 (1H, d, J=3 Hz), 4.27 (1H, d, J=3 Hz)

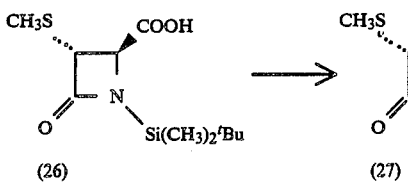

(26)      (27)

In 12 ml of methanol was dissolved 569 mg of compound (26) and 3 ml of 1N hydrochloric acid was added to the solution. The mixture was stirred for 1.75 hours at room temperature. The reaction solution was cooled to 0° C. and 3 ml of 1N sodium hydroxide was added thereto. The mixture was concentrated to dryness under reduced pressure. The residue was dissolved in water and the aqueous solution was lyophilized to obtain white powders containing (2R,3R)-3-methylthio-4-oxo-2-azetidinecarboxylic acid (27). The powders were used in the following example without purifying them.

EXAMPLE 8

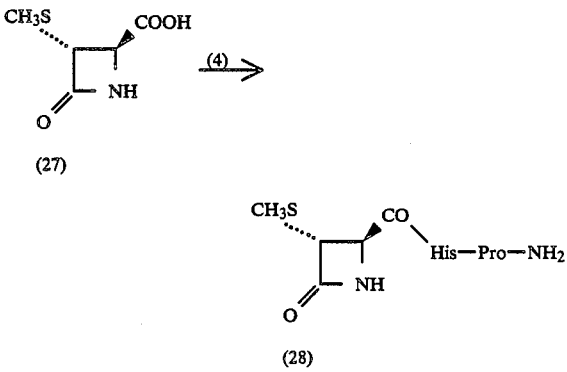

(28)

The white powders containing compound (27) obtained in Reference Example 6(b) were dissolved in a mixture of 5 ml of DMF and 5 ml of methylene chloride and, 324 mg of HOBT was added to the solution. Then, 618 mg of DCC was added thereto under ice-cooling and the mixture was stirred for 40 minutes at the same temperature.

To the reaction mixture was added a DMF solution of 2 mmols of L-histidyl-L-prolinamide (free base) prepared in a manner similar to Example 7.

After stirring at 0° to 5° C. overnight, insoluble matters were filtered off. The filtrate was concentrated under reduced pressure. The thus obtained oily substance was subjected to column chromatography using 100 g of silica gel. By eluting with a mixture of chloroform-methanol-ammonia water (80:20:2), N$^\alpha$-[(2R,3R)-3-methylthio-4-oxo-2-azetidinylcarbonyl]-L-histidyl-L-prolinamide (28) was obtained. After lyophilization, 236 mg of the product was obtained as a colorless solid.

(i) m.p. 142°~144° C.

(ii) NMR (d$^6$-DMSO) δppm: 1.85 (4H, m), 2.06 (3H, s, S—CH$_3$), 2.84~2.96 (2H, m), 6.93 (1H, s), 6.98 (1H), 7.56 (1H, s), 8.04 (1H), 8.5 (2H, m)

(iii) IR (KBr) cm$^{-1}$: 3400 (broad), 1755, 1620~1680 (broad)

(iv) Mass (m/z) FAB: 395 (M+1), 381, 349

REFERENCE EXAMPLE 7

(Raw Material of Example 9)

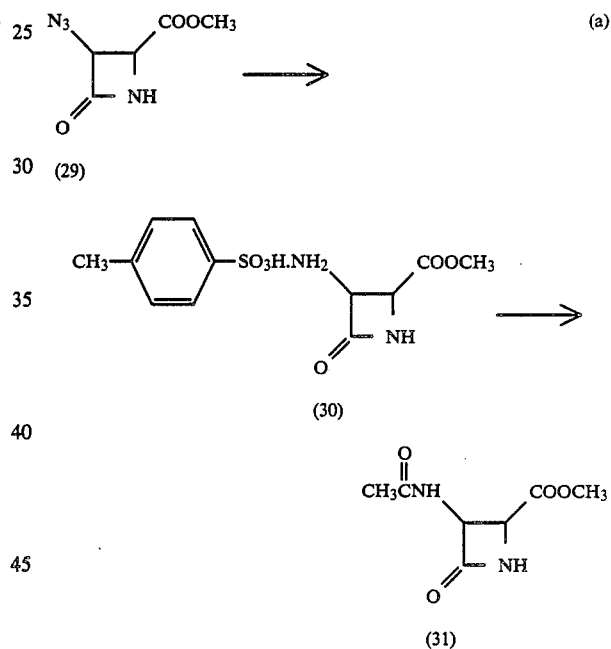

In 50 ml of DMF were dissolved 1.67 g of methyl (±)cis-3-azido-4-oxo-2-azetidinecarboxylate (29) and 1.86 g of p-toluenesulfonic acid monohydrate and, 400 mg of 10% Pd-C was added to the solution followed by hydrogenation at ambient temperature under atmospheric pressure of hydrogen. The catalyst was filtered off and the solvent was removed by distillation under reduced pressure to obtain a viscous oil. The oil was dissolved in 80 ml of methylene chloride. The solution was cooled to −10° C. and, 2.89 ml of triethylamine and 0.736 ml of acetyl chloride were added to the solution in sequence. The mixture was stirred at the same temperature for 1 hour and 20 minutes. The reaction mixture was concentrated under reduced pressure and the residue was subjected to column chromatography using 100 g of silica gel. By eluting with ethyl acetate-methanol (10:1), 683 mg of methyl (±)cis-3-acetylamino-4-oxo-2-azetidinecarboxylate (31) was obtained as a white solid.

(i) NMR (CDCl$_3$+CD$_3$OD) δppm: 1.98 (3H, s, CH$_3$CO), 3.77 (3H, s, OCH$_3$), 4.46 (1H, d, J=6 Hz), 5.45 (1H, d, J=6 Hz)

(ii) IR (KBr) cm$^{-1}$: 3250, 3175, 3080, 1745, 1650

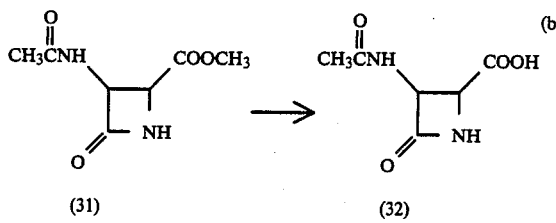

In 40 ml of methanol was dissolved 497 mg of compound (31) and 2.7 ml of 1N sodium hydroxide was added to the solution under ice cooling. Stirring was performed for 25 minutes under ice cooling and then for 30 minutes after removing a cooling bath. The solution was again ice-cooled and 2.7 ml of 1N hydrochloric acid was added to the solution. The mixture was concentrated to dryness under reduced pressure. The residue was azeotropically dehydrated with an acetonitrile-benzene mixture under reduced pressure to obtain the residue containing (±)cis-3-acetylamino-4-oxo-2-azetidinecarboxylic acid (32). This substance was used in the following example as it was.

EXAMPLE 9

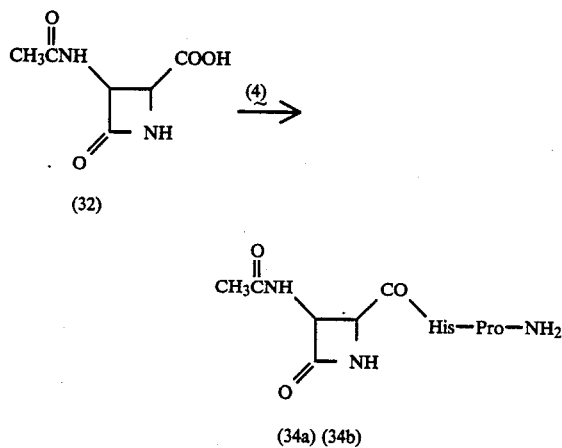

The residue containing compound (32) obtained in Reference Example 7 was reacted with L-histidyl-L-prolinamide (free base) in a similar manner as above. The thus obtained reaction mixture was purified by column chromatography using silica gel (150 g). The desired compound was eluted with ethyl acetate-methanol-ammonia water (20:10:1). After the solvent was removed, the product was lyophilized. Thus, 274 mg was obtained as a mixture of N$^\alpha$-[(2S,3S)-3-acetylamino-4-oxo-2-azetidinylcarbonyl]-L-histidyl-L-prolinamide (34a) and N$^\alpha$-[(2R,3R)-3-acetylamino-4-oxo-2-azetidinylcarbonyl]-L-histidyl-L-prolinamide (34b).

(i) NMR (D$_2$O) δppm: 1.88~2.10 (7H), 2.95~3.16 (2H), 3.5 (1H, m), 3.8 (1H, m), 4.4 (1H, m), 4.57 (1H, m), 4.7~5.04 (1H, m), 5.35 (1H, m), 7.08 (1H), 7.88 (1H)

(ii) IR (KBr) cm$^{-1}$: 3350 (broad), 1755, 1620~1680 (broad)

Mass (m/z) FAB: 406 (M+1), 363, 235

REFERENCE EXAMPLE 8

(Raw Material of Example 10)

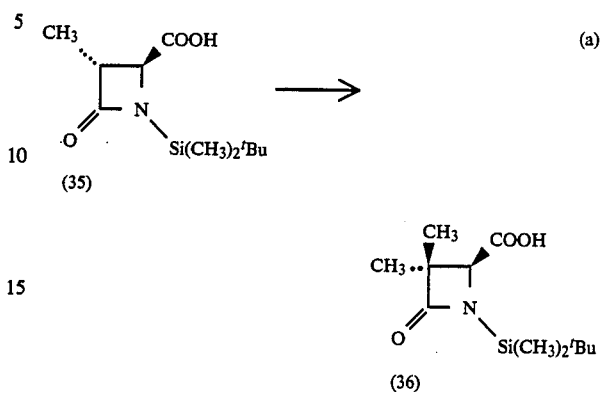

A solution of 1.98 g of diisopropylamine in 10 ml of THF was dropwise added to 12.3 ml of a hexane solution of 1.59 mols of n-butyl lithium in an atmosphere of argon under ice cooling. The reaction was performed at the same temperature for 15 minutes. The solution was cooled to −78° C. and, 2.19 g of (2S, 3R)-1-t-butylidimethylsilyl-3-methyl-2-azetidine-carboxylic acid (35) was added to the solution. The mixture was reacted at −78° C. for 30 minutes and then at 0° C. for 30 minutes. To the reaction mixture was dropwise added a solution of 1.53 g of methyl iodide in 10 ml of THF. The mixture was reacted at 0° C. for 30 minutes and then at 10° to 15° C. for 30 minutes.

After completion of the reaction, 22.5 ml of a 10% citric acid aqueous solution was added to the reaction mixture under ice cooling. Thereafter the mixture was extracted with 60 ml of ether.

The organic layer was extracted with 48 ml of a saturated hydrogen sodium carbonate aqueous solution. To the aqueous layer was added 6 g of citric acid under ice cooling followed by extracting with 60 ml of chloroform. After the organic layer was dried over anhydrous sodium sulfate, the solvent was removed by distillation. The solid residue was washed with hexane to obtain 1.19 g of powdery (S)-1-t-butyldimethylsilyl-3,3-dimethyl-4-oxo-2-azetidinecarboxylic acid (36).

(i) NMR (CDCl$_3$) δppm: 6.40~6.90 (1H, OH), 3.84 (1H, s), 1.44 (3H, s,

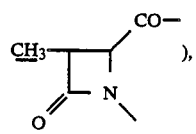

), 1.21 (3H, s,

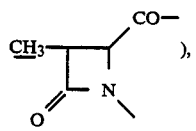

), 0.98 (9H, s, t-Bu), 0.34 (3H, s, Si—CH$_3$), 0.14 (3H, s, Si—CH$_3$)

(ii) [α]$_D^{25}$ −47.2° (C=0.75, methanol)

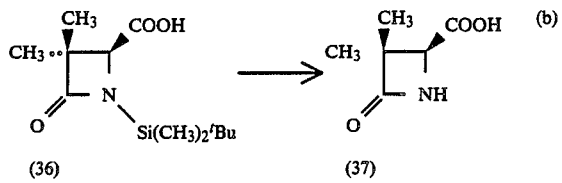

To a mixture of 4.5 ml of 1N hydrochloric acid and 18 ml of methanol was added 730 mg of compound (36). The reaction was performed for 2 hours at room temperature. After completion of the reaction, 4.5 ml of a 1N sodium hydroxide aqueous solution was added to the reaction mixture under ice cooling. The solvent was removed by distillation under reduced pressure and further azeotropically dehydrated with toluene to obtain white powder containing (S)-3,3-dimethyl-4-oxo-2-azetidinecarboxylic acid (37). This was used as a raw material in Example 10 as it was.

EXAMPLE 10

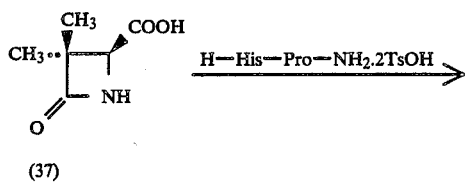

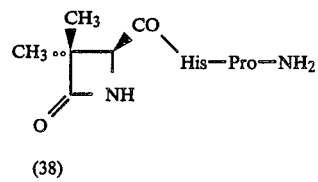

In 15 ml of DMF was dissolved the white powder containing compound (37) obtained in Reference Example 8(b). Under ice cooling, 426 mg of HOBT and 743 mg of DCC were added to the solution and the reaction was performed for 30 minutes under ice cooling (reaction solution A).

On the other hand, 1.79 g of L-histidyl-L-prolinamide di-p-toluenesulfonate was dissolved in 15 ml of DMF. The solution was cooled to −20° to −30° C. and 668 mg of triethylamine was added to the solution. The reaction was performed at the same temperature for 30 minutes to obtain a DMF solution containing L-histidyl-L-prolinamide (reaction solution B). Reaction solution B was added to reaction solution A under ice cooling. The mixture was reacted at 0° to 5° C. overnight. Insoluble matters were filtered off and the solvent was removed by distillation under reduced pressure. The thus obtained residue was subjected to column chromatography using silica gel.

By eluting with chloroform-methanol-ammonia water (90:10:1), 650 mg of N$^\alpha$-[(S)-3,3-dimethyl-4-oxo-2-azetidinylcarbonyl]-L-histidyl-L-prolinamide (38) was obtained as a white foam.

(i) NMR (D$_2$O) δppm: 7.72 (1H,

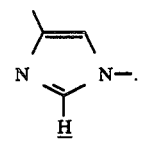

7.05 (1H,

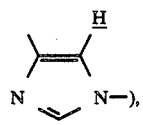

4.28∼4.54 (1H), 3.44∼4.20 (3H), 4.04 (1H, s,

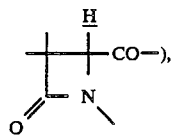

2.92∼3.20 (2H), 1.72∼2.48 (4H, m), 1.38 (3H, s, CH$_3$), 0.86 (3H, s, CH$_3$)

(ii) IR (KBr) cm$^{-1}$: 3250, 2950, 2850, 1740, 1665, 1630, 1540, 1520

(iii) Mass (m/z): 376 (M$^+$), 263, 235, 190, 165, 110, 70

EXAMPLE 11

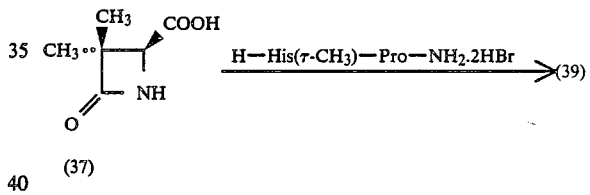

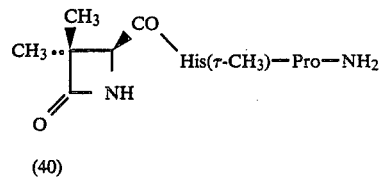

Compound (37) was obtained by treating 442 mg of compound (36) in a manner similar to Reference Example 8(b). To a solution of compound (37) in 8.6 ml of DMF were added 244 mg of HOBT and 425 mg of DCC under ice-cooling. The reaction was performed at the same temperature for 1 hour (reaction solution A).

On the other hand, 734 mg of N$^\tau$-methyl-L-histidyl-L-prolinamide dihydrobromide (39) was dissolved in 8.6 ml of DMF. After the solution was cooled to −20° to −30° C., 366 mg of triethylamine was added thereto. The reaction was performed at the same temperature for 30 minutes.

The formed insoluble matters were filtered off to obtain a DMF solution containing τ-methyl-L-histidyl-L-prolinamide (reaction solution B).

Reaction solution B was added to reaction solution A. The reaction was performed at 0°∼5° C. for 3 days. The insoluble materials were filtered off and the solvent was removed from the filtrate by distillation under reduced pressure. The residue was subjected to column chromatography using silica gel. By eluting with chloroform-methanol-ammonia water (90:10:1), 547 mg of N$^\alpha$-[(S)-3,3-dimethyl-4-oxo-2-azetidinylcarbonyl]-$\tau$-methyl-L-histidyl-L-prolinamide (40) was obtained as a white foam.

(i) NMR (D$_2$O) δppm: 7.57 (1H,

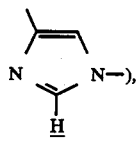

7.01 (1H,

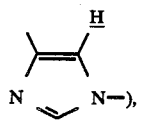

4.29~4.53 (1H), 4.03 (1H, s,

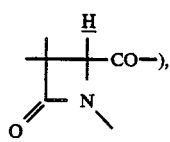

3.64 (3H, s, N—CH$_3$), 3.43~4.17 (6H in total), 2.73~3.10 (2H), 1.72~2.48 (4H, m), 1,37 (3H, s, C—CH$_3$), 0.82 (3H, s, C—CH$_3$)

(ii) Mass (m/z): 390 (M+), 277, 249, 179, 124, 70

(iii) [α]$_D^{22}$ −47.0° (C=0.98, methanol)

PREPARATION EXAMPLES

Injection

A lyophilized formulation containing 0.025 mg or 0.05 mg of N$^\alpha$-[(2S, 3R)-3-azido-4-oxo-2-azetidinylcarbonyl]-L-histidyl-L-prolinamide together with 10 ml of mannitol in one ampoule was prepared and each of the formulations was dissolved in 1 ml of a sterilized physiological saline solution to provide an injection.

Tablets

A mixture of 0.25 part by weight of N$^\alpha$-[(2S,3R)-3-azido-4-oxo-2-azetidinylcarbonyl]-L-histidyl-L-prolinamide and 7.5 parts by weight of lactose was pulverized, and mixed uniformly with 44.4 parts by weight of lactose, 22.5 parts by weight of crystalline cellulose, and 0.4 part by weight of magnesium stearate. The resultant mixture was compacted to form tablets of 75 mg/tablet.

Capsules

A mixture of 0.5 part by weight of N$^\alpha$-[(2S,3R)-3-azido-4-oxo-2-azetidinylcarbonyl]-L-histidyl-L-prolinamide and 10 parts by weight of lactose was pulverized, and mixed uniformly with 137.5 parts by weight of lactose, 60 parts by weight of corn starch and 2.0 parts by weight of magnesium stearate. The mixture was filled into gelatin hard capsules to provide capsulated preparations of 210 mg/capsule.

What is claimed is:

1. A substituted azetidinone compound shown by the formula (I):

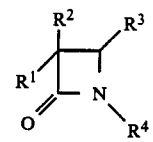

wherein one of $R^1$ and $R^2$ represents a hydroxy lower alkyl group, a phenyl lower alkyl group, an azido group, an amino group, a lower alkanoyl amino group, a mercapto group or a lower alkylthio group and the other represents a hydrogen group, or, both represent a hydrogen atom or a lower alkyl group; $R^3$ represents a hydrogen atom or a group shown by the formula:

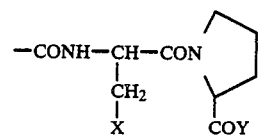

wherein X represents

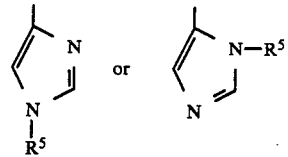

wherein $R^5$ represents a hydrogen atom or a lower alkyl group and Y represents a hydroxy group, a lower alkoxy group, an amino group, a mono- or di-lower alkylamino group; $R^4$ represents a hydrogen atom, lower alkyl group, a hydroxy lower alkyl group or a group shown by the formula: —CH$_2$CO—A wherein A represents an amino group or a group shown by formula:

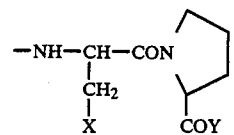

wherein X and Y are as defined above, provided that when $R^1$ and $R^2$ are the same or different and each is a hydrogen atom or a methyl group, $R^4$ represents a group other than a hydrogen atom or methyl; and provided that when $R^3$ is a hydrogen atom, $R^4$ is a group shown by formula —CH$_2$CO—A; and when $R^4$ is a hydrogen atom, $R^3$ is a group shown by formula

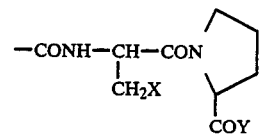

wherein A, X and Y are as defined above, or a salt thereof.

2. A compound as claimed in claim 1, wherein in the formula (I) $R^1$ is a phenyl lower alkyl group, a lower alkanoyl group, an azido group, a lower alkylthio group or a lower alkanoyl amino group; $R^2$ is a hydrogen atom; $R^3$ is as defined in claim 1; and $R^4$ is a hydrogen atom or a hydroxy lower alkyl group.

3. A compound as claimed in claim 1, wherein in the formula (I) $R^1$ is an azido group; and $R^2$, $R^3$ an $R^4$ are as defined in claim 1.

4. A compound as claimed in claim 1, which is selected from the group consisting of:

$N^\alpha$-[(S)-1-Hydroxymethyl-4-oxo-2-azetidinylcarbonyl]-L-histidyl-L-prolinamide, $N^\alpha$-[(3S,4S)-3-(1-Hydroxyethyl-4-oxo-2-azetidinylcarbonyl]-L-histidyl-L-prolinamide, $N^\alpha$-[(2S,3R)-3-Benzyl-4-oxo-2-azetidinylcarbonyl]-L-histidyl-L-prolinamide, $N^\alpha$-[(2S,3R)-3-Azido-4-oxo-2-azetidinylcarbonyl]-L-histidyl-L-prolinamide, $N^\alpha$-[(2R,3R)-3-Methylthio-4-oxo-2-azetidinylcarbonyl]-L-histidyl-L-prolinamide, $\tau$-Methyl-$N^\alpha$-[(2S,3R)-3-methyl-4-oxo-2-azetidinylcarbonyl]-L-histidyl-L-prolinamide, and $N^\alpha$-[(S)-3,3-Dimethyl-4-oxo-2-azetidinylcarbonyl]-$\tau$-methyl-L-histidyl-L-prolinamide.

5. A compound as claimed in claim 1, wherein in the formula (I) $R^1$ and $R^2$ are a hydrogen atom; $R^3$ is as defined in claim 1; and $R^4$ is a hydroxy lower alkyl or unsubstituted lower alkyl group other than methyl or a group shown by formula —$CH_2COA$, wherein A is as defined in claim 1.

6. A compound as claimed in claim 1, wherein in the formula (I) $R^1$ and $R^2$ are a lower alkyl group; and $R^3$ and $R^4$ are as defined in claim 1.

7. A medicament formulation which has a beneficial action on the central nervous system, said formulation comprised of, in single dose form, from 0.001 to 10 milligrams of the azetidinone compound of claim 1, and a pharmaceutically acceptable carrier.

* * * * *